(12) United States Patent
Shimuta

(10) Patent No.: US 12,338,377 B2
(45) Date of Patent: Jun. 24, 2025

(54) STICKING COMPONENT

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 326 days.

(21) Appl. No.: 18/066,644

(22) Filed: Dec. 15, 2022

(65) Prior Publication Data

US 2023/0121455 A1    Apr. 20, 2023

Related U.S. Application Data

(63) Continuation of application No. PCT/JP2021/013621, filed on Mar. 30, 2021.

(30) Foreign Application Priority Data

Jul. 22, 2020  (JP) .................................. 2020-125057

(51) Int. Cl.
*A61B 5/01*        (2006.01)
*A61B 5/00*        (2006.01)
(Continued)

(52) U.S. Cl.
CPC .................. *C09J 7/403* (2018.01); *A61B 5/01* (2013.01); *A61B 5/68335* (2017.08); *C09J 7/22* (2018.01);
(Continued)

(58) Field of Classification Search
CPC ........... A61B 5/00; A61B 5/0008; A61B 5/01; A61B 5/6832; A61B 5/6833;
(Continued)

(56) References Cited

U.S. PATENT DOCUMENTS 9,580,626 B2 *   2/2017   Colby ......................... C09J 7/40
2011/0152738 A1   6/2011   Zepeda et al.
(Continued)

FOREIGN PATENT DOCUMENTS

JP    H1178389 A    3/1999
JP    2000160111 A    6/2000
(Continued)

OTHER PUBLICATIONS

International Search Report in PCT/JP2021/013621, mailed Jun. 22, 2021, 4 pages.

*Primary Examiner* — Michael A Tolin
(74) *Attorney, Agent, or Firm* — ArentFox Schiff LLP

(57) ABSTRACT

A sticking component that includes: a sheet-shaped adhesive component having first and second sticking surfaces with adhesiveness opposed to each other, the first sticking surface constructed to be removably adhered to a bottom surface of a stick-on biometric device; a first release component removably adhered to the first sticking surface of the sticking component; and a second release component removably adhered to the second sticking surface of the sticking component, wherein at least one of the first release component or the second release component has an outline that is visible, and that, when the sticking component is to be adhered to the stick-on biometric device, at least partially overlaps an outline of the bottom surface of the stick-on biometric device in a plan view of the sticking component.

9 Claims, 5 Drawing Sheets

(51) Int. Cl.
*B32B 37/26* (2006.01)
*C09J 7/22* (2018.01)
*C09J 7/40* (2018.01)

(52) U.S. Cl.
CPC ... *B32B 2037/268* (2013.01); *B32B 2307/402* (2013.01); *B32B 2307/41* (2013.01); *B32B 2307/412* (2013.01); *C09J 2203/37* (2020.08); *C09J 2301/124* (2020.08)

(58) Field of Classification Search
CPC ........... A61B 5/68335; A61F 13/00085; A61F 13/02; B32B 27/281; B32B 27/32; B32B 27/36; B32B 2037/268; B32B 2307/402; B32B 2307/4026; B32B 2307/41; B32B 2307/412; B32B 2307/414; C09J 7/203; C09J 7/22; C09J 7/38; C09J 7/40; C09J 7/403; C09J 2203/37; C09J 2301/124; G01K 1/14
See application file for complete search history.

(56) References Cited

U.S. PATENT DOCUMENTS

| | | |
|---|---|---|
| 2017/0136648 A1 | 5/2017 | Grader et al. |
| 2018/0243141 A1* | 8/2018 | Park .................. A61F 13/00085 |
| 2019/0046033 A1* | 2/2019 | Gannon .................. G01K 1/024 |
| 2019/0261923 A1 | 8/2019 | Talgorn et al. |
| 2020/0309608 A1 | 10/2020 | Shimuta et al. |

FOREIGN PATENT DOCUMENTS

| | | |
|---|---|---|
| JP | 2013501591 A | 1/2013 |
| JP | 2017529114 A | 10/2017 |
| JP | 2018509191 A | 4/2018 |
| JP | 2019537470 A | 12/2019 |
| JP | 2020078440 A | 5/2020 |
| WO | 2019131203 A1 | 7/2019 |

* cited by examiner

STICKING COMPONENT

CROSS REFERENCE TO RELATED APPLICATIONS

The present application is a continuation of International application No. PCT/JP2021/013621, filed Mar. 30, 2021, which claims priority to Japanese Patent Application No. 2020-125057, filed Jul. 22, 2020, the entire contents of each of which are incorporated herein by reference.

FIELD OF THE INVENTION

The present invention relates to a sticking component. More specifically, the present invention relates to a sticking component that is to be adhered to a stick-on biometric device used by being adhered to a living body.

BACKGROUND OF THE INVENTION

Various stick-on biometric devices used by being adhered to a living body have been proposed in the related art. To use such a stick-on biometric device, that is, to stick the stick-on biometric device to the body surface (skin) of a living body for use, for example, a release liner on the sticking surface (adhesive surface) is removed, and then the stick-on biometric device is adhered to the body surface of the living body.

For example, Patent Document 1 discloses a sticking component described below. The sticking component includes a first sticking layer, an intermediate layer, a second sticking layer, a film-shaped release component, and a tab. One sticking surface of the first sticking layer is to be adhered to a stick-on biometric device. One surface of the intermediate layer is adhered to the other sticking surface of the first sticking layer. One sticking surface of the second sticking layer is adhered to the other surface of the intermediate layer. The release component is adhered to the other sticking surface of the second sticking layer. The tab protrudes from an outer edge portion of the release component. The release component of the sticking component has a slit around the basal end portion of the tab. The slit extends inward from the outer edge of the release component.

Patent Document 1: Japanese Unexamined Patent Application Publication No. 2020-078440

SUMMARY OF THE INVENTION

The release component mentioned above is designed so that, as the user pulls on the tab to remove the release component from the second sticking layer, a relatively small region (minute portion) of the release component that is defined by the slit peels off first, and then the main body of the release component begins to peel off. This helps to mitigate concentration of stress on an end portion of the intermediate layer, and reduce potential intra-layer delamination of the intermediate layer or inter-layer delamination. As the user grasps the tab and peels off the release component, the release component can be removed in one removal motion. As a result, when removing the release component to stick the stick-on biometric device to the living body, the user is able to easily remove the release component in one removal motion without causing intra-layer delamination or inter-layer delamination.

If, for instance, the stick-on biometric device is a stick-on body thermometer, to prevent inaccurate body temperature measurements, the bottom surface (undersurface) of the thermometer with a built-in temperature sensor needs to be adhered to the skin in a manner that ensures close contact with no gap therebetween. At this time, if the sticking position of the sticking component is greatly misaligned relative to the bottom surface of the thermometer, a situation can arise in which, for example, the bottom surface in a portion of the thermometer where the temperature sensor is built-in (or in the vicinity of the portion) fails to stick to the skin, the sticking component becomes wrinkled, or the sticking component becomes doubled-over at its end portion. This may result in a gap being created between the skin and the bottom surface in the portion of the thermometer where the temperature sensor is built-in (or in the vicinity of the portion), which in turn may potentially reduce the accuracy of body temperature measurement. A need therefore exists to minimize misalignment of the sticking position of the sticking component relative to the stick-on biometric device.

The present invention is directed to addressing the above-mentioned problem. Accordingly, it is an object of the present invention to provide a sticking component that is to be adhered to a stick-on biometric device used by being adhered to a living body, and that makes it possible to, when the sticking component is to be adhered to the stick-on biometric device, facilitate alignment of the sticking position and reduce potential misalignment of the sticking position.

A sticking component according to the present invention includes: a sheet-shaped adhesive component having first and second sticking surfaces with adhesiveness opposed to each other, the first sticking surface constructed to be removably adhered to a bottom surface of a stick-on biometric device; a first release component removably adhered to the first sticking surface of the sticking component; and a second release component removably adhered to the second sticking surface of the sticking component, wherein at least one of the first release component or the second release component has an outline that is visible, and that, when the sticking component is to be adhered to the stick-on biometric device, at least partially overlaps an outline of the bottom surface of the stick-on biometric device in a plan view of the sticking component.

According to the above-mentioned configuration of the sticking component according to the present invention, at least one of the first release component or the second release component has an outline that is visible, and that is capable of, when the sticking component is to be adhered to the stick-on biometric device, at least partially overlapping an outline of the bottom surface of the stick-on biometric device in plan view. This allows the user to easily align the sticking component through visual inspection, by aligning the visible outline (contour) of the at least one of the first release component or the second release component with the bottom surface of the stick-on biometric device in an overlapping relationship.

The present invention thus makes it possible to, when the sticking component is to be adhered to the stick-on biometric device, facilitate alignment of the sticking position, and reduce potential misalignment of the sticking position.

DETAILED DESCRIPTION OF THE PREFERRED EMBODIMENTS

Figure 1:
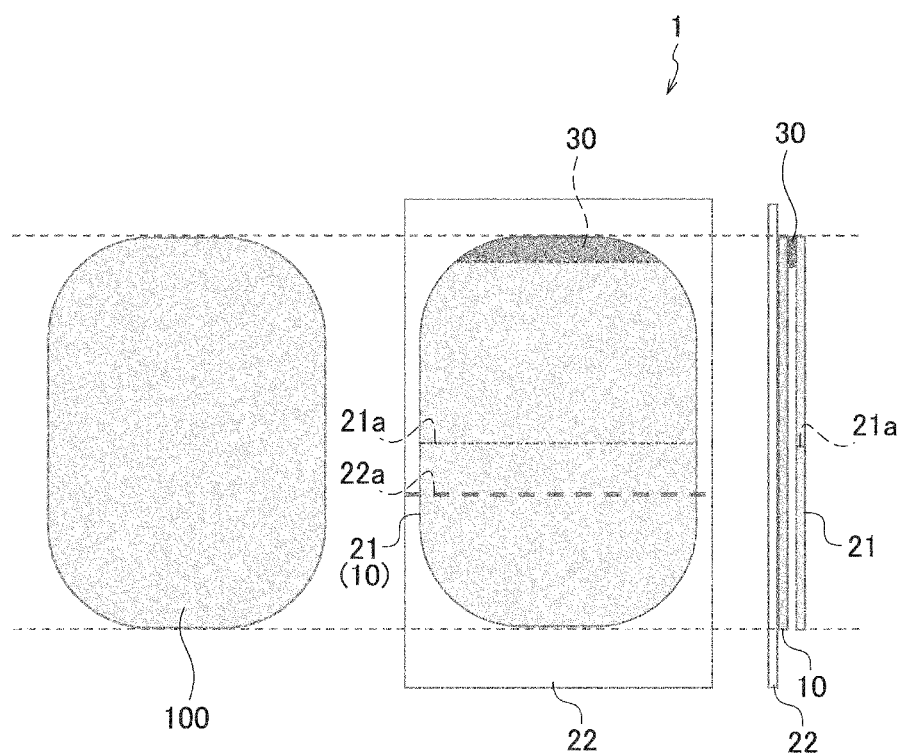
FIG. 1 illustrates, in plan and side elevation views, a sticking component according to an embodiment.

A preferred embodiment of the present invention is described below in detail with reference to the drawings. In the drawings, identical or corresponding features are identified with identical reference signs. In the drawings, identical elements are designated by identical reference signs to avoid repetitive description.

First, reference is made to FIG. 1 to describe a configuration of a sticking component 1 according to an embodiment. FIG. 1 illustrates, in plan and side elevation views, the sticking component 1 according to the embodiment. The following description is directed to an exemplary application of the present invention to a stick-on deep-body thermometer 100 (which corresponds to a stick-on biometric device as recited in the claims, and will be referred to simply as "deep-body thermometer 100" hereinafter). Accordingly, the bottom surface of the deep-body thermometer 100 is also depicted in FIG. 1. A suitable example of the deep-body thermometer 100 may be the deep-body thermometer described in International Publication No. 2019/225532.

The sticking component 1 includes the following major components: an adhesive component 10 having a pair of sticking surfaces (front and back surfaces) with adhesiveness; a first release component 21 removably adhered to a first sticking surface of the adhesive component 10; and a second release component operation button 22 removably adhered to a second sticking surface of the adhesive component 10 opposite the first sticking surface. The sticking component 1 is a laminate of the first release component 21, the adhesive component 10, and the second release component 22.

To use the sticking component 1, the first release component 21 adhered to the first sticking surface of the adhesive component 10 is removed, and the first sticking surface is adhered to the bottom surface (lower exterior body) of the deep-body thermometer 100 in a removable (peelable) manner. Further, the second release component 22 adhered to the second sticking surface of the adhesive component 10 is removed, and the second sticking surface is adhered to a living body.

The adhesive component 10 is sheet-shaped, and has a pair of sticking surfaces with adhesiveness. In use, a first of the pair of sticking surfaces of the adhesive component 10 is removably adhered to the bottom surface of the deep-body thermometer 100. According to the embodiment, the adhesive component 10 has a substantially rectangular shape with four rounded corners, that is, the same shape as that of the bottom surface of the deep-body thermometer 100. The adhesive component 10 is identical in dimensions (size) to the bottom surface of the deep-body thermometer 100.

To ensure that the sticking component 1 (adhesive component 10) does not rip (tear) easily when removed from the bottom surface of the sticking component 1 after use of the deep-body thermometer 100, the adhesive component 10 is preferably in the form of, for example, a doubled-sided tape including the following components: a core made of a resin film; and an adhesive layer disposed on each surface of the core. Suitable examples of the adhesive component 10 (adhesive layer) may include acrylic-based adhesives and silicone-based adhesives. Other suitable examples may include synthetic rubber-based adhesives. The adhesive component 10 has a thickness of preferably 0.005 mm to 1.0 mm, more preferably 0.05 mm to 0.3 mm.

In this case, the adhesive component 10 includes the core made of a resin film as described above. This helps to prevent the adhesive component 10 from ripping and remaining on the deep-body thermometer 100 as the adhesive component 10 is removed from the bottom surface of the deep-body thermometer 100 after use of the deep-body thermometer 100.

The first release component 21 is a film-shaped (or sheet-shaped) component that is adhered to the first sticking surface of the adhesive component 10 during, for example, storage to thereby protect the first sticking surface so that the sticking surface does not decrease in adhesiveness as a result of dust or other contaminants adhering to the first sticking surface. The first release component 21 is peeled off from the first sticking surface of the adhesive component 10 when the deep-body thermometer 100 is to be used (when the sticking component 1 is to be adhered to the deep-body thermometer 100).

Likewise, the second release component 22 is a film-shaped (or sheet-shaped) component that is adhered to the second sticking surface of the adhesive component 10 when the deep-body thermometer 100 is not in use (e.g., during storage). The second release component 22 is peeled off from the second sticking surface of the adhesive component 10 when the deep-body thermometer 100 is to be used (when the deep-body thermometer 100 is to be adhered to a living body to measure deep body temperature).

At least one of the first release component 21 or the second release component 22 has a visible outline (contour). More specifically, at least one of the first release component 21 or the second release component 22 is made of, for example, an opaque material or a colored transparent material.

At least one of the first release component 21 or the second release component 22 has an outline (contour) that is capable of, when the sticking component 1 is to be adhered to the bottom surface of the deep-body thermometer 100, at least partially overlapping (being made to coincide with) the outline (contour) of the bottom surface of the deep-body thermometer 100 in plan view. More specifically, at least one of the first release component 21 or the second release component 22 has an outline (contour) that is capable of overlapping the outline (contour) of the bottom surface of the deep-body thermometer 100, for example, in the respective straight sections of at least two intersecting sides of the bottom surface (or at three points).

According to the embodiment, the first release component 21 has an outline (contour) that is visible (opaque), and that is capable of, when the sticking component 1 is to be adhered to the deep-body thermometer 100, overlapping the outline (contour) of the bottom surface of the deep-body thermometer 100 in plan view (as viewed in the direction of thickness). That is, the first release component 21 is identical in shape and dimensions (size) to the bottom surface of the deep-body thermometer 100. The second release component 22 is made of a colorless transparent material.

More specifically, the first release component 21 (paper separator) is made of, for example, opaque paper. According to the embodiment, the first release component 21 has a substantially rectangular shape with four rounded corners. Further, the outline (contour) of the first release component 21 has the same size as (coincides with) the outline (contour) of the bottom surface of the deep-body thermometer 100. This allows the user to easily stick the sticking component 1 without misalignment by aligning the bottom surface of the deep-body thermometer 100 and the outline (contour) of the first release component 21 through visual inspection. At this time, the alignment can be performed through visual inspection because the second release component 22 described later is made of transparent PET.

In another example, only the outline (contour) of the first release component 21 may be opaque. In still another example, only a portion of the outline (contour) that overlaps (coincides with) the outline of the deep-body thermometer 100 may be opaque.

The first release component 21 is preferably divided into multiple (two in FIG. 1) portions by a cut 21a extending substantially parallel to the short sides of the first release component 21. This configuration allows the user to easily stick the sticking component 1 to the bottom surface of the deep-body thermometer 100 without misalignment in a manner as described below. First, through visual inspection, the user aligns the first release component 21 with the bottom surface of the deep-body thermometer 100 (i.e., aligns the outline (contour) of the first release component 21 with the outline (contour) of the bottom surface of the deep-body thermometer 100). Then, for example, the user holds fingers against the upper halves of both the sticking component 1 and the bottom surface of the deep-body thermometer 100 to ensure that the sticking component 1 and the deep-body thermometer 100 do not become misaligned. In this state, the user removes the lower half of the first release component 21, and sticks the lower half of the sticking component 1 to the bottom surface of the deep-body thermometer 100. Subsequently, the user holds fingers against the lower halves of both the sticking component 1 and the bottom surface of the deep-body thermometer 100. The user then removes the upper half of the first release component 21, and sticks the upper half of the sticking component 1 to the bottom surface of the deep-body thermometer 100. That is, the user sticks the sticking component 1 to the bottom surface of the deep-body thermometer 100 by removing the first release component 21, which is divided into two portions, half by half.

The second release component 22 (PET separator) is made of, for example, colorless transparent polyethylene terephthalate (PET). More specifically, suitable examples of the second release component 22 include a PET film to which release treatment has been applied. It is to be noted, however, that the second release component 22 may be made of any hard resin, such as biaxially-oriented polypropylene (BOPP) or polyimide (PI). The second release component 22 has a thickness of preferably 0.025 mm to 0.3 mm, more preferably 0.05 mm to 0.2 mm.

According to the embodiment, the second release component 22 has a rectangular shape. In plan view, the second release component 22 preferably has an outline (contour) that is at least partially larger than the outline of the adhesive component 10 (the bottom surface of the deep-body thermometer 100). This allows the user to easily remove the second release component 22 by grasping a portion of the second release component 22 that extends beyond (i.e., protrudes beyond) the outline of the adhesive component 10 (the bottom surface of the deep-body thermometer 100), with no separate tab or other such structure required.

In particular, according to the embodiment (the example illustrated in FIG. 1), the second release component 22 has an outline that, across its entire perimeter, is (generally) larger than the outline of the adhesive component 10 (the bottom surface of the deep-body thermometer 100). This allows the user to remove the second release component 22 by grasping anywhere on the outer edge of the second release component 22 that protrudes beyond the adhesive component 10, irrespective of the direction of grasping or the direction of removal. Another conceivable situation where the above configuration may be useful is when multiple sticking components 1 are stacked. In this case, the adhesive component 10 may protrude out beyond the first release component 21 from the sides of one sticking component 1, which may cause vertically adjacent sticking components 1 to adhere. Even if this occurs, the second release component 22 is larger than the adhesive component 10 as described above, and thus the user can grasp the second release component 22 to easily separate the sticking components 1 that are adhering to each other.

The second release component 22 is preferably divided into multiple (two in FIG. 1) portions by a perforation, a half-cut, or a fold 22a (to be referred to as "perforation or other separation line 22a" hereinafter). In this case, with the second release component 22 removed up to the perforation or other separation line 22a, the user first aligns the deep-body thermometer 100 with a target object (living body), and sticks the deep-body thermometer 100 to the target object in this state. Subsequently, the user removes the entire second release component 22, and sticks the entire deep-body thermometer 100 to the target object. In this way, the user is able to stick the deep-body thermometer 100 without misalignment.

The location of the perforation or other separation line 22a may preferably be determined so that, with the second release component 22 removed up to the perforation or other separation line 22a, the adhesive component 10 has such an exposed area that allows the deep-body thermometer 100 to be fixed to the target object (living body) while still allowing for re-sticking. If positioning the perforation or other separation line 22a in a middle portion of the second release component 22 allows the above-mentioned condition to be met, then it is desired to position the perforation or other separation line 22a in the middle portion. Such positioning is desired for the ability to easily remove the second release component 22 in whichever desired direction. It is to be noted, however, that if positioning the perforation or other separation line 22a in the middle portion of the second release component 22 results in an adhesion that is too strong to allow re-sticking, then the location of the perforation or other separation line 22a is preferably changed in accordance with desired requirements or other factors. In that case, it is preferred to make removal easier in one direction than in another, or provide multiple perforations or other separation lines 22a. That is, it is preferred to provide multiple perforations or other separation lines 22a so that the second release component 22 may be removed in whichever of upward and downward directions.

Further, it is preferred that a non-adhesive, film-shaped release strip 30 be partially sandwiched between one sticking surface of the adhesive component 10 and the first release component 21. The release strip 30 is disposed on, for example, an end portion of the adhesive component 10 (first release component 21). Suitable exemplary materials for the release strip 30 include PET and hard resin (such as BOPP or PI). The release strip 30 has a thickness of preferably 0.005 mm to 0.3 mm, more preferably 0.05 mm to 0.2 mm. This ensures that the adhesion decreases locally in the area where the non-adhesive release strip 30 is disposed in a sandwiched fashion. As a result, after use of the deep-body thermometer 100, the adhesive component 10 can be easily removed from the bottom surface of the deep-body thermometer 100.

Preferably, to increase visibility, the release strip 30 is colored and transparent (color-tinted) or is opaque. In this case, the release strip 30 is colored (or opaque), which allows for easy visibility of the release strip 30 when the user removes the adhesive component 10 from the deep-body thermometer 100 after use. This facilitates removal of the adhesive component 10.

Due to the configuration mentioned above, when the deep-body thermometer 100 is to be used (when the sticking component 1 is to be adhered to the deep-body thermometer 100), the first release component 21 adhered to the adhesive component 10 is removed, and then the sticking component 1 (adhesive component 10) is adhered to the bottom surface of the deep-body thermometer 100.

More specifically, first, through visual inspection, the user aligns the sticking component 1 (first release component 21) with the bottom surface of the deep-body thermometer 100 (i.e., aligns the outline (contour) of the first release component 21 with the outline (contour) of the bottom surface of the deep-body thermometer 100). Then, while holding the upper halves of both the sticking component 1 and the bottom surface of the deep-body thermometer 100 with fingers of one hand (e.g., the thumb and the index finger of the left hand) to prevent misalignment between the deep-body thermometer 100 and the sticking component 1, the user grasps a lower portion of the first release component 21 with fingers of the other hand (e.g., the thumb and the index finger of the right hand), and removes the lower half of the first release component 21 divided into two portions. The user then sticks the sticking component 1 (adhesive component 10) with the first release component 21 removed to the bottom surface of the deep-body thermometer 100. Subsequently, in a similar manner, while holding the lower halves of both the sticking component 1 and the bottom surface of the deep-body thermometer 100 with fingers of one hand (e.g., the thumb and the index finger of the left hand), the user grasps an upper portion of the first release component 21 with fingers of the other hand (e.g., the thumb and the index finger of the right hand), and removes the upper half of the first release component 21 divided into two portions. The user then sticks the entirety (the remainder) of the sticking component 1 (adhesive component 10) to the bottom surface of the deep-body thermometer 100.

Subsequently, when sticking the deep-body thermometer 100 to a living body to measure deep body temperature, the user grasps the outer edge of the second release component 22 with fingers, and peels off the second release component 22 adhered to the other sticking surface of the sticking component 1 (adhesive component 10). The user then sticks the deep-body thermometer 100 to the body surface (skin) of the user (subject). More specifically, as described above, with the second release component 22 removed up to the perforation or other separation line 22a, the user aligns the deep-body thermometer 100 with the target object (living body), and sticks the deep-body thermometer 100 to the target object in this state. Then, the user removes the entire second release component 22, and sticks the entire deep-body thermometer 100 to the target object.

In this way, the sticking component 1 can be adhered to the deep-body thermometer 100 (or replaced) easily and without misalignment, and the deep-body thermometer 100 can be adhered to the user's skin.

As described above in detail, according to the embodiment, the first release component 21 has an outline (contour) that is visible (opaque), and that is capable of, when the sticking component 1 is to be adhered to the deep-body thermometer 100, overlapping the outline (contour) of the bottom surface of the deep-body thermometer 100 in plan view. This allows the user to easily align the sticking component 1 through visual inspection, by aligning the visible outline (contour) of the first release component 21 with the bottom surface of the deep-body thermometer 100 in an overlapping relationship. This in turn makes it possible to, when the sticking component 1 is to be adhered to the deep-body thermometer 100, facilitate alignment of the sticking position, and reduce potential misalignment of the sticking position.

First Modification

The foregoing description of the embodiment is directed to a configuration in which the release strip 30, which is a non-adhesive film-shaped strip, is sandwiched partially between one sticking surface of the adhesive component 10, and the first release component 21. In an alternative configuration, instead of the release strip 30, a portion of the first release component 21 is allowed to remain on the adhesive component 10 upon sticking of the sticking component 1 to the deep-body thermometer 100, so that this portion of the first release component 21 serves as a non-adhesive film-shaped release strip (a remaining strip of the first release component 21) that is sandwiched partially between the one sticking surface of the adhesive component 10 and the bottom surface of the deep-body thermometer 100.

Figure 2:
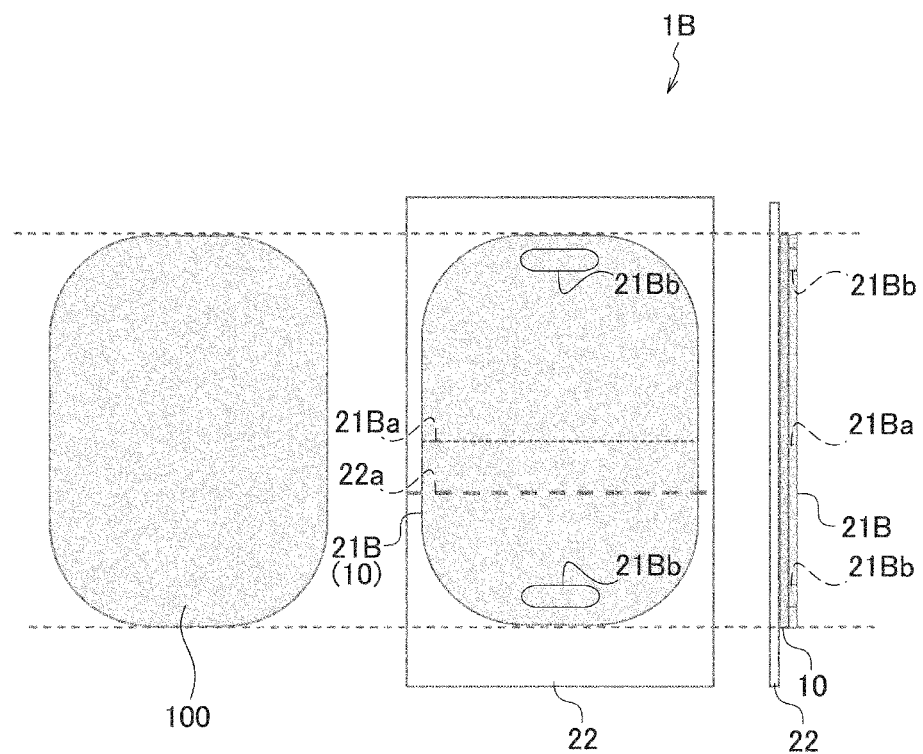
FIG. 2 illustrates, in plan and side elevation views, a sticking component according to a first modification of the embodiment.

Reference is now made to FIG. 2 to describe a sticking component 1B according to a first modification of the embodiment. FIG. 2 illustrates, in plan and side elevation views, the sticking component 1B according to the first modification. The sticking component 1B differs from the sticking component 1 according to the above-mentioned embodiment in that the sticking component 1B does not include the release strip 30, and that the sticking component 1B includes, instead of the first release component 21, a first release component 21B with a slit 21Bb.

The first release component 21B includes a region (release strip) that is defined by the slit 21Bb, and that remains on one sticking surface of the adhesive component 10 upon removal of the first release component 21B. The slit 21Bb is a closed slit that is not in contact with the outer perimeter of the first release component 21B. Accordingly, after the adhesive component 10 is adhered to the deep-body thermometer 100, this release strip is sandwiched between the adhesive component 10, and a portion of the deep-body thermometer 100 near the outer edge of the deep-body thermometer 100.

More specifically, the slit (cut) 21Bb preferably has a closed shape that is not in contact with the outer edge of the first release component 21B, for example, an ellipse or a rounded rectangle. The slit 21Bb is preferably separated from the outer edge of the first release component 21B by, for example, 2 mm or more to prevent tearing upon removal of the first release component 21B. Multiple (two in FIG. 2) such slits 21Bb may be provided. The sticking component 1B is otherwise identical or similar in configuration to the sticking component 1 according to the embodiment mentioned above, and thus will not be herein described in further detail.

According to the first modification, upon removal of the first release component 21B, a portion (release strip) of the first release component 21B that is enclosed by the slit 21Bb with a closed shape remains on the adhesive component 10, and the release strip is sandwiched partially between one sticking surface of the adhesive component 10 and the bottom surface of the deep-body thermometer 100. The area where the release strip is sandwiched between these surfaces thus has locally reduced adhesion, which allows for easy removal of the sticking component 1B after use of the deep-body thermometer 100.

Second Modification

Figure 3:
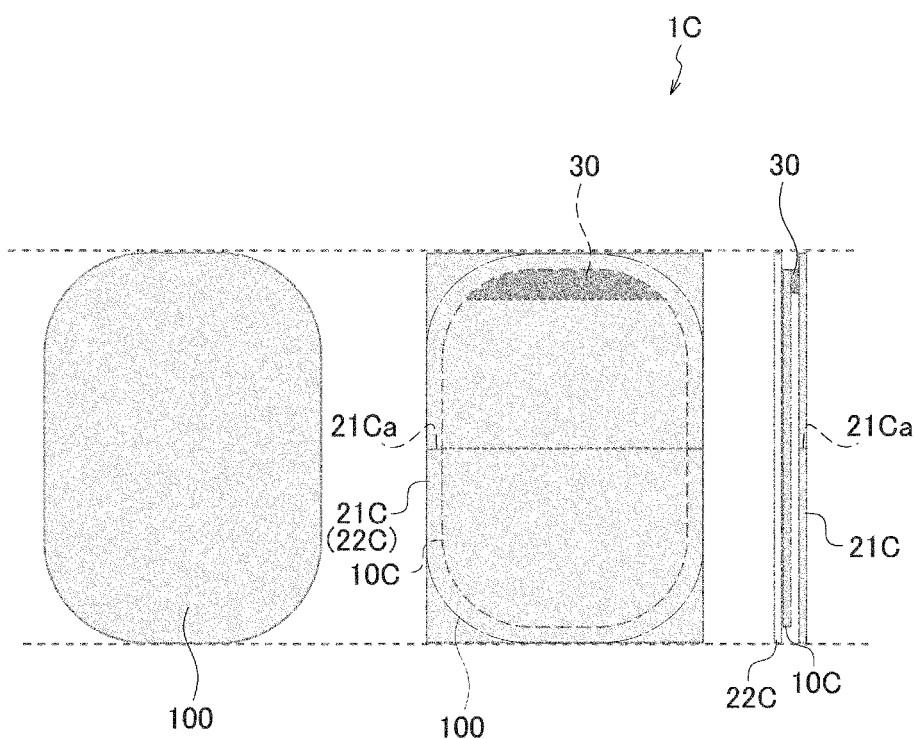
FIG. 3 illustrates, in plan and side elevation views, a sticking component according to a second modification of the embodiment.

Reference is now made to FIG. 3 to describe a sticking component 1C according to a second modification of the embodiment. FIG. 3 illustrates, in plan and side elevation views, the sticking component 1C according to the second modification.

The sticking component 1C differs from the sticking component 1 according to the embodiment mentioned above in the following respects: the sticking component 1C includes a first release component 21C instead of the first release component 21: the sticking component 1C includes a second release component 22C instead of the second release component 22; and the sticking component 1C includes an adhesive component 10C instead of the adhesive component 10.

The first release component 21C differs from the first release component 21 in that the first release component 21C has a rectangular shape. In this case, the first release component 21C preferably has an outline (contour) that overlaps the respective straight sections of at least two intersecting sides of the bottom surface of the deep-body thermometer 100. According to the second modification, the first release component 21C has an outline (contour) that overlaps the respective straight sections of four sides of the bottom surface of the deep-body thermometer 100 (as indicated by alternate long and short dashed lines in FIG. 3).

The second release component 22C differs from the second release component 22 in that the second release component 22C is smaller in dimensions (size) than the second release component 22. According to the second modification, the second release component 22C is identical in shape and dimensions (size) to the first release component 21C. In this case, it is preferred that at least a portion of the outline (contour) of the second release component 22C be larger than (i.e., protrude beyond) the outline of the adhesive component 10C (the bottom surface of the deep-body thermometer 100). According to the second modification, the corner sections (four corners) of the second release component 22C protrude beyond the adhesive component 10C (the bottom surface of the deep-body thermometer 100). This allows the user to easily remove the second release component 22C by grasping a portion of the second release component 22C that protrudes beyond the adhesive component 10C (the bottom surface of the deep-body thermometer 100), with no separate tab or other such structure required.

The adhesive component 10C differs from the adhesive component 10 described above in that the adhesive component 10C is smaller in dimensions (size) than the adhesive component 10. That is, the outline of the adhesive component 10C has dimensions smaller than those of the outline (contour) of the bottom surface of the deep-body thermometer 100. Alternatively, the adhesive component 10C may have the same dimensions as those of the outline of the bottom surface of the deep-body thermometer 100. In that case, the first release component 21C may likewise have the same outline (dimensions) as that of the adhesive component 10C (the bottom surface of the deep-body thermometer 100). The sticking component 1C is otherwise identical or similar in configuration to the sticking component 1 according to the embodiment mentioned above, and thus will not be herein described in further detail.

According to the second modification as well, the user is able to stick the sticking component 1C to the bottom surface of the deep-body thermometer 100 easily and without misalignment by pressing, against the user's fingers for positioning, (at least two) (four according to the second modification) areas where the bottom surface of the deep-body thermometer 100 and the outline (contour) of the first release component 21C overlap.

Third Modification

Figure 4:
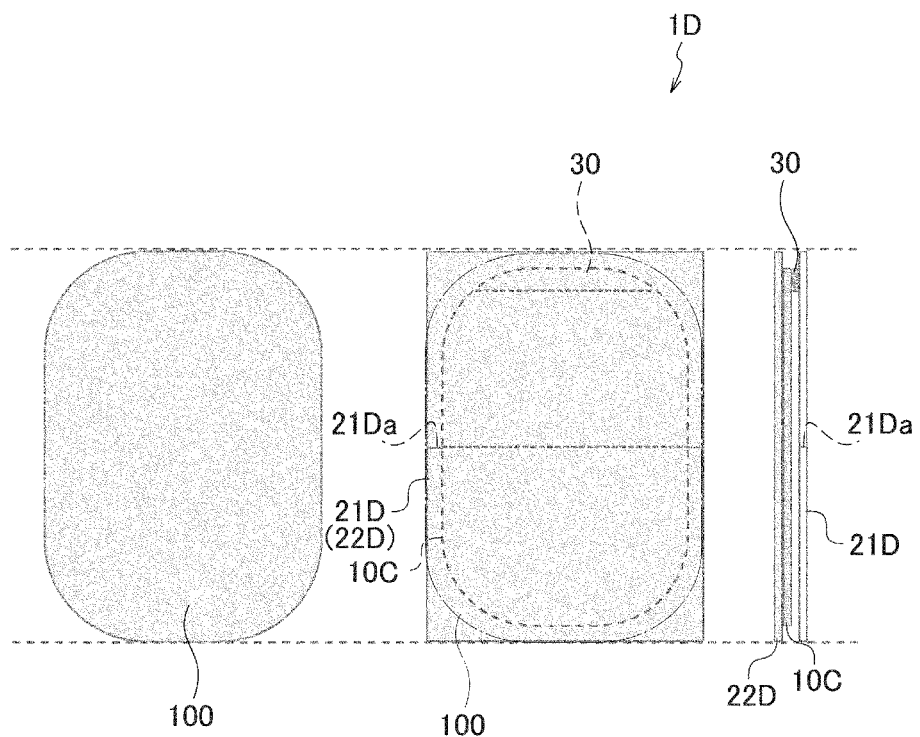
FIG. 4 illustrates, in plan and side elevation views, a sticking component according to a third modification of the embodiment.

According to the second modification mentioned above, the first release component 21C is opaque, and the second release component 22C is transparent. Alternatively, the first release component 21 may be transparent, and the second release component 22C may be opaque. Reference is now made to FIG. 4 to describe a sticking component 1D according to a third modification of the embodiment. FIG. 4 illustrates, in plan and side elevation views, the sticking component 1D according to the third modification.

The sticking component 1D differs from the sticking component 1C according to the second modification mentioned above in that the sticking component 1D includes a transparent first release component 21D instead of the opaque first release component 21, and that the sticking component 1D includes an opaque second release component 22D instead of the transparent second release component 22C.

The first release component 21D is preferably made of, for example, colorless transparent PET. By contrast, the second release component 22D is preferably made of, for example, opaque paper. According to the third modification, the first release component 21D and the second release component 22D are identical to each other in shape and dimensions (size).

In this case, the second release component 22D preferably has an outline (contour) that overlaps the respective straight sections of at least two intersecting sides of the bottom surface of the deep-body thermometer 100. According to the third modification, the second release component 22D has an outline (contour) that overlaps the respective straight sections of four sides of the bottom surface of the deep-body thermometer 100 (as indicated by alternate long and short dashed lines in FIG. 4). The sticking component 1D is otherwise identical or similar in configuration to the sticking component 1C according to the second modification mentioned above, and thus will not be herein described in further detail.

According to the third modification, the user is able to stick the sticking component 1D to the bottom surface of the deep-body thermometer 100 easily and without misalignment by pressing, against the user's fingers for positioning, (at least two) (four according to the third modification) areas where the bottom surface of the deep-body thermometer 100 and the outline (contour) of the second release component 22D overlap.

Fourth Modification

Figure 5:
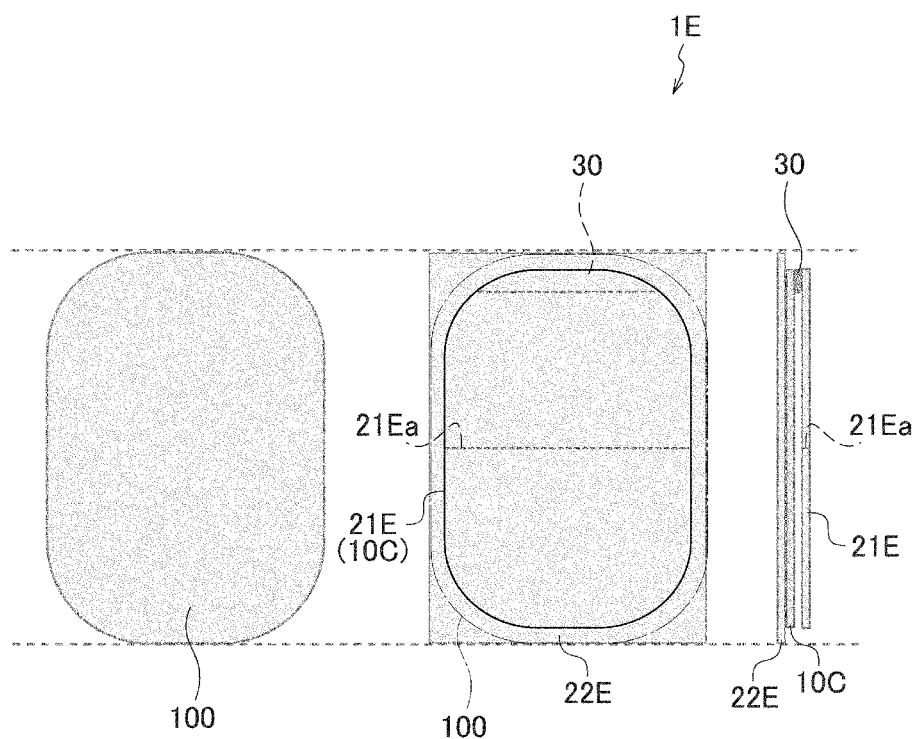
FIG. 5 illustrates, in plan and side elevation views, a sticking component according to a fourth modification of the embodiment.

According to the second modification mentioned above, the first release component 21C is opaque, and the second release component 22C is transparent. Alternatively, the first release component 21 may be opaque, and the second release component 22C may be also opaque. Reference is now made to FIG. 5 to describe a sticking component 1E according to a fourth modification of the embodiment. FIG. 5 illustrates, in plan and side elevation views, the sticking component 1E according to the fourth modification.

The sticking component 1E differs from the sticking component 1C according to the second modification mentioned above in that the sticking component 1E includes a first release component 21E instead of the first release component 21C, and that the sticking component 1E includes an opaque second release component 22E instead of the second release component 22C.

The first release component 21E is preferably made of, for example, opaque paper. The first release component 21E differs from the first release component 21C mentioned above in that the first release component 21E is smaller in dimensions (size) than the first release component 21C. According to the fourth modification, the first release component 21E is identical in shape and dimensions (size) to the adhesive component 10C.

The second release component 22E is likewise made of, for example, opaque paper. In this case as well, the second release component 22E preferably has an outline (contour) that overlaps the respective straight sections of at least two intersecting sides of the bottom surface of the deep-body thermometer 100. According to the fourth modification, the second release component 22E has an outline (contour) that overlaps the respective straight sections of four sides of the bottom surface of the deep-body thermometer 100 (as indicated by alternate long and short dashed lines in FIG. 5). The sticking component 1E is otherwise identical or similar in configuration to the sticking component 1C according to the second modification mentioned above, and thus will not be herein described in further detail.

According to the second modification as well, the user is able to stick the sticking component 1E to the bottom surface of the deep-body thermometer 100 easily and without misalignment by pressing, against the user's fingers for positioning, (at least two) (four according to the fourth modification) areas where the bottom surface of the deep-body thermometer 100 and the outline (contour) of the second release component 22E overlap.

Although an embodiment of the present invention has been described above, it is to be understood that the present invention is not limited to the embodiment described above but may accommodate various modifications. For example, although the foregoing description of the embodiment is directed to an exemplary application of the present invention to the deep-body thermometer 100, the present invention may be applicable to thermometers other than such a deep-body thermometer. Further, the present invention may be applicable to, for example, electrocardiogramd stick-on biometric devices used to measure breathing, pulse, or other vital signs.

The size, positioning, number, and other specific details of the above-mentioned components and features, such as the first release component 21, the second release component 22, the adhesive component 10, the slit 21Bb, the cut 21a, and the perforation or other separation line 22a, are not limited to those exemplified in the above embodiment but may be determined as appropriate based on desired requirements or other factors.

REFERENCE SIGNS LIST 1, 1B, 1C, 1D, 1E sticking component
10, 10C adhesive component
21, 21B, 21C, 21D, 21E first release component
22, 22C, 22D, 22E second release component
21a, 21Ba, 21Ca, 21Da, 21Ea cut
21Bb slit
22a perforation, half-cut, or fold
30 release strip
100 deep-body thermometer (stick-on biometric device)

The invention claimed is:

1. A sticking component comprising:
a sheet-shaped adhesive component having first and second sticking surfaces with adhesiveness opposed to each other, the first sticking surface constructed to be removably adhered to a bottom surface of a stick-on biometric device;
a first release layer removably adhered to the first sticking surface of the sheet-shaped adhesive component; and
a second release layer removably adhered to the second sticking surface of the sheet-shaped adhesive component,
wherein at least one of the first release layer or the second release layer has an outline that is visible, and that, when the sheet-shaped adhesive component is to be adhered to the stick-on biometric device, at least partially overlaps an outline of the bottom surface of the stick-on biometric device in a plan view of the sticking component, and
wherein the first release layer includes at least one region that is defined by a slit, and that, upon removal of the first release layer, the at least one region remains on the first sticking surface of the adhesive component, the slit being a closed slit and not in contact with an outer perimeter of the first release layer.

2. The sticking component according to claim 1, wherein at least one of the first release layer or the second release layer is made of an opaque material or a colored transparent material.

3. The sticking component according to claim 1, wherein at least one of the first release layer or the second release layer has an outline that, when the sheet-shaped adhesive component is to be adhered to the stick-on biometric device, overlaps the outline of the bottom surface of the stick-on biometric device in the plan view in respective straight sections of at least two sides of the bottom surface.

4. The sticking component according to claim 1,
wherein the first release layer has an outline that is visible, and that, when the sheet-shaped adhesive component is to be adhered to the stick-on biometric device, at least partially overlaps the outline of the bottom surface of the stick-on biometric device in the plan view, and
wherein the second release layer is made of a colorless transparent material, and has an outline that is at least partially larger than an outline of the adhesive component.

5. The sticking component according to claim 1, wherein the first release layer is divided by a cut line into a plurality of portions.

6. The sticking component according to claim 1, wherein the adhesive component includes a core made of a resin film, and respective adhesive layers disposed on opposite sides of the core.

7. The sticking component according to claim 1, wherein the second release layer is divided by a perforation, a cut, or a fold into a plurality of portions.

8. The sticking component according to claim 1, wherein a release strip is sandwiched partially between the first sticking surface of the adhesive component and the first release layer, the release strip being non-adhesive and film-shaped.

9. The sticking component according to claim 8, wherein the release strip is colored and transparent, or is opaque.

* * * * *